United States Patent [19]

Langlois et al.

[11] Patent Number: 5,604,261
[45] Date of Patent: Feb. 18, 1997

[54] NEW ARYLALKYL (THIO)AMIDES

[75] Inventors: Michel Langlois, Sceaux; Pierre Renard, Versailles; Gérard Adam, Le Mesnil le Roi, all of France

[73] Assignee: Adir Et Compagnie, Courbevoie, France

[21] Appl. No.: 446,323

[22] Filed: May 22, 1995

Related U.S. Application Data

[62] Division of Ser. No. 375,503, Jan. 18, 1995, Pat. No. 5,464,872, which is a continuation of Ser. No. 131,207, Oct. 1, 1993, abandoned.

[30] Foreign Application Priority Data

Oct. 2, 1992 [FR] France ................. 92 11671

[51] Int. Cl.⁶ .................. A61K 31/16; C07C 233/05
[52] U.S. Cl. .................. 514/630; 514/252; 514/255; 514/256; 514/307; 514/311; 514/357; 514/427; 514/438; 514/471; 514/522; 514/563; 514/629; 514/423; 564/215; 564/218; 564/221; 564/219; 564/220
[58] Field of Search .................. 564/215, 219, 564/218, 221, 220; 514/630, 629, 522, 563, 427, 438, 471, 357, 255, 256, 252, 311, 307, 923

[56] References Cited

U.S. PATENT DOCUMENTS 3,944,675 3/1976 Symchowicz et al. .................. 424/324
5,059,620 10/1991 Stout et al. .................. 514/422
5,194,614 3/1993 Andrieux et al. .................. 544/400
5,225,442 7/1993 Andrieux et al. .................. 514/628

FOREIGN PATENT DOCUMENTS 0238868 9/1987 European Pat. Off. .

*Primary Examiner*—Shailendra Kumar
*Attorney, Agent, or Firm*—The Firm of Gordon W. Hueschen

[57] ABSTRACT

A compound which is selected from those of formula (I):

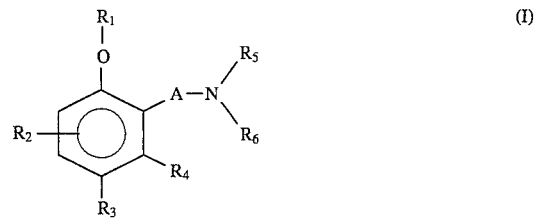

in which A, $R_1$, $R_2$, $R_3$, $R_4$, $R_5$ and $R_6$ are as defined in the description, its optical isomers, and its addition salts thereof with a pharmaceutically-acceptable acid or base, and medicinal products containing the same which are useful for treating a disorder of the melatoninergic system.

6 Claims, No Drawings

NEW ARYLALKYL (THIO)AMIDES

The present application is a division of our prior-filed application Ser. No. 08/375,503, filed Jan. 18, 1995, now U.S. Pat. No. 5,464,872 which in turn is a continuation of our prior-filed application Ser. No. 08/131,207, filed Oct. 1, 1993, now abandoned.

The application relates to new arylalkyl(thio)amides, to a process for preparing them and to pharmaceutical compositions containing them.

Application EP 238,868 has already described compounds of phenylalkylamide structure, presenting them as tyrosine kinase inhibitors and antitumor and antibacterial agents.

Many studies have demonstrated the major role of melatonin (5-methoxy-N-acetyltryptamine) in the control of the circadian rhythm and the endocrine functions, and the melatonin receptors have been characterized and localized. The practitioner hence has a real need for compounds that have an action on the melatoninergic system.

The Applicant discovered that new compounds of arylalkyl(thio)amide structure, substituted on their benzene ring with a hydroxyl or alkoxy radical specifically at the ortho position with respect to the alkyl(thio)amide chain, possessed very considerable activity with respect to the melatoninergic system, whereas these properties are not encountered with compounds substituted at the meta or para position with respect to the alkyl(thio)amide chain.

More especially, the present invention relates to the compounds of formula (I):

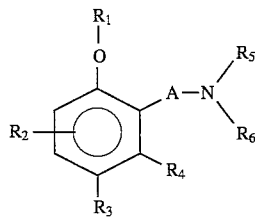

in which:

A represents a —CH$_2$-CH$_2$— chain, unsubstituted or substituted with a lower alkyl, R$_1$ represents a hydrogen atom or a lower alkyl, R$_2$ represents a hydrogen atom, a halogen atom or a lower alkyl, R$_3$ and R$_4$, which may be identical or different, each represent, independently of one another, a radical chosen from:
hydrogen,
halogen,
lower alkyl,
cyano,
carboxyl,
nitro,
amino,
lower alkylamino,
lower dialkylamino,
—(CH$_2$)$_n$—E$_1$ in which n represents 0 or an integer from 1 to 4, and E$_1$ represents a cycloalkyl or a cycloalkenyl and contains from 3 to 8 carbon atoms, E$_1$ being unsubstituted or substituted with one or more radicals chosen from halogen, oxo and lower alkyl,
and —(CH$_2$)$_{n'}$—E$_2$ in which n' represents 0 or an integer from 1 to 4 and E$_2$ represents a radical chosen from: phenyl, naphthyl, pyrrolyl, thienyl, furyl, pyridyl, pyrazinyl, pyrimidinyl, pyridazinyl, quinolyl and isoquinolyl, E2 being unsubstituted or substituted with one or more radicals chosen from: halogen, hydroxyl, lower alkyl, lower alkoxy and trifluoromethyl, or R$_3$ and R$_4$, together with the benzene ring which carries them, form a ring-system E$_3$ chosen from: indene, naphthalene, benzothiophene, benzofuran, indole, benzimidazole, benzopyran, benzothiopyran, quinoline, isoquinoline, indazole, quinoxaline, quinazoline, cinnoline, benzothiazole, benzisothiazole, benzoxazole, benzisoxazole, benzoxazine, benzothiazine, benzodioxole and benzodioxane, on the understanding that the portion of the ring-system E$_3$ formed by R$_3$ and R$_4$ and the two carbon atoms of the benzene ring which carry them is:
unhydrogenated or partially hydrogenated,
and unsubstituted or substituted with one or more radicals chosen from: halogen, hydroxyl, lower alkyl, lower alkoxy, lower alkoxycarbonyl and trifluoromethyl, R$_5$ represents a hydrogen atom or a lower alkyl, R$_6$ represents a group

in which X represents a sulfur
or oxygen atom and R$_7$ represents a radical chosen from:
lower alkyl, unsubstituted or substituted with one or more radicals chosen from halogen, hydroxyl and lower alkoxy,
linear or branched alkenyl having 2 to 7 carbon atoms, unsubstituted or substituted with one or more radicals chosen from halogen, hydroxyl and lower alkoxy,
and —(CH$_2$)$_m$—E$_4$ in which m represents 0 or an integer from 1 to 4 and E$_4$ represents a mono- or bicyclic cycloalkyl having 3 to 12 carbon atoms, unsubstituted or substituted with one or more radicals chosen from halogen, oxo and lower alkyl, with the proviso that R$_7$ can represent a lower alkyl, unsubstituted or substituted with one or more radicals chosen from halogen, hydroxyl and lower alkoxy, only if R$_3$ and R$_4$ form a ring-system E$_3$ as defined above with the benzene ring which carries them, or if one of the substituents R$_3$ and R$_4$ represents a lower alkyl and the other substituent R$_3$ or R$_4$ represents a hydrogen atom, their optical isomers, and their addition salts with a pharmaceutically acceptable acid or base when R$_3$ or R$_4$ represents a salifiable group, on the understanding that she terms "lower alkyl" and "Lower alkoxy" denote linear or branched groups having 1 to 6 carbon atoms and that the terms "cycloalkenyl" and "alkenyl" denote hydrocarbon groups containing one or more double bonds.

The invention also encompasses:
the compounds according to the formula (I) in which R$_3$ and R$_4$, together with the benzene ring which carries them, form a ring-system E$_3$ chosen from: indene, naphthalene, benzothiophene, benzofuran, indole, benzimidazole, benzopyran, benzothiopyran, quinoline, isoquinoline, indazole, quinoxaline, quinazoline, cinnoline, benzothiazole, benzisothiazole, benzoxazole, benzisoxazole, benzoxazine, benzothiazine, benzodioxole and benzodioxane, on the understanding that the portion of the ring-system E$_3$ formed by R$_3$ and R$_4$ and the 2 carbon atoms of the benzene ring which carry them is:
unhydrogenated or partially hydrogenated,
and unsubstituted or substituted with one or more radicals chosen from: halogen, hydroxyl, lower alkyl, lower alkoxy, lower alkoxycarbonyl and trifluoromethyl, the compounds according to the formula (I) in which R$_3$ and R$_4$, together with the benzene ring which carries them, form a naphthalene, on the understanding that the benzene ring formed by $R_3$, $R_4$ and the 2 carbon atoms which carry them is unsubstituted or substituted with one or more radicals chosen from halogen, hydroxyl, lower alkyl, lower alkoxy, lower alkoxycarbonyl and trifluoromethyl, and the compounds according to the formula (I) in which $R_1$ represents a methyl radical and $R_3$ and $R_4$, together with the benzene ring which carries them, form a naphthalene, on the understanding that the benzene ring formed by $R_3$ and $R_4$ and the 2 carbon atoms which carry them is unsubstituted or substituted with one or more radicals chosen from: halogen, hydroxyl, lower alkyl, lower alkoxy, lower alkoxycarbonyl and trifluoromethyl.

Among pharmaceutically acceptable acids which may be used to form an addition salt with the compounds of she invention, hydrochloric, sulfuric, phosphoric, tartaric, malic, maleic, fumaric, oxalic, methanesulfonic, ethanesulfonic, campboric and citric acids may be mentioned as examples and without implied limitation.

Among pharmaceutically acceptable bases which may be used to salify the compounds used according to the invention, sodium hydroxide, potassium hydroxide, triethylamine, diethylamine, ethanolamine, arginine, lysine and diethanolamine may be mentioned as examples and without implied limitation.

The invention also encompasses the process for preparing the compounds of formula (I), wherein:

a compound of formula (II) :

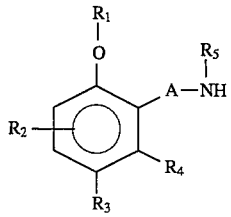
(II)

in which A, $R_1$, $R_2$, $R_3$, $R_4$ and $R_5$ are as defined in the formula (I), is reacted with a compound of formula (III):

(III)

or of formula (IV):

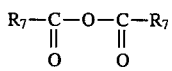
(IV)

in which formulae $R_7$ is as defined in the formula (I) and Hal represents a halogen atom, to obtain a compound of formula (I/a):

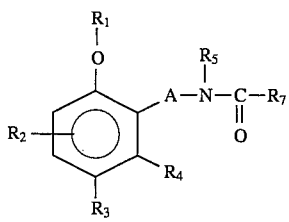
(I/a)

in which A, $R_1$, $R_2$, $R_3$, $R_4$, $R_5$ and $R_7$ are as defined above, which compound of formula (I/a) is subjected to Lawesson's reagent in order to obtain the compound of formula (I/b):

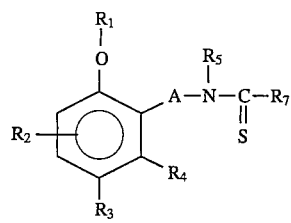
(I/b)

in which A, $R_1$, $R_2$, $R_3$, $R_4$, $R_5$ and $R_7$ are as defined above, the compounds of formulae (I/a) and (I/b) forming the set of compounds of formula (I), it being possible for the compounds of formula (I) to be:
 purified according to one or more purification methods chosen from crystallization, chromatography on a silica column, gas chromatography, extraction, filtration and passage through charcoal or resin,
 separated, where appropriate, in pure form or in the form of a mixture, into their possible optical isomers,
 or salified with a pharmaceutically acceptable acid or base.

The starting compounds used in the process for preparing the compounds of formula (I) are:
either commercially available
or readily accessible to a person skilled in the art using processes contained in the literature.

The compounds of formula (II) are, in particular, readily accessible to a person skilled in the art, when A represents an ethylene moiety, by reducing a compound of formula (II/a):

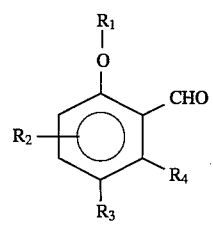
(II/a)

in which $R_1$, $R_2$, $R_3$ and $R_4$ are as defined in the formula (I), to obtain a compound of formula (II/b):

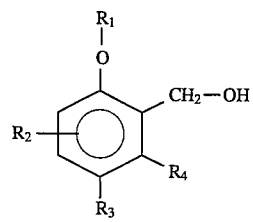
(II/b)

in which $R_1$, $R_2$, $R_3$ and $R_4$ are as defined above, which is then subjected to a halogenating agent to obtain a compound of formula (II/c):

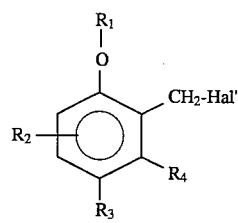
(II/c)

in which $R_1$, $R_2$, $R_3$ and $R_4$ are as defined adore and Hal' represents a halogen atom, which compound of formula (II/c) is reacted with potassium cyanide in order to obtain the compound of formula (II/d):

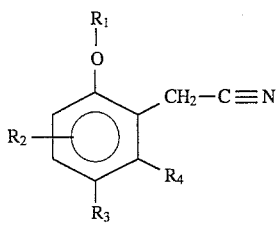 (II/d)

in which $R_1$, $R_2$, $R_3$ and $R_4$ as defined above, in which gives, after hydrogenation, the compound of formula (II/e):

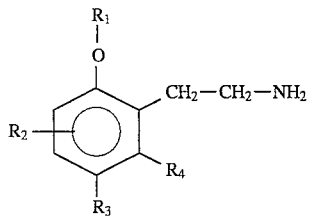 (II/e)

in which $R_1$, $R_2$, $R_3$ and $R_4$ are as defined above, which compound of formula (II/e) can be, where appropriate, reacted with a compound of formula (V):

 (V)

Hal"—$R_5$' in which $R_5$, represents a linear or branched alkyl having 1 to 6 carbon atoms and Hal" represents a halogen atom, to obtain the compound of formula (II/e'):

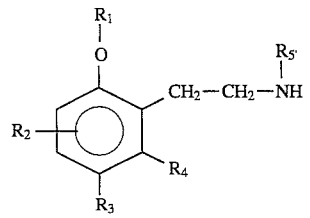 (II/e')

in which $R_1$, $R_2$, $R_3$, $R_4$ and $R_5$' are as defined above, the compounds of formulae (II/e) and (II/e') forming the set of compounds of formula (II), it being possible for the compounds of formula (II) to be:

purified according to one or more purification methods chosen from crystallization, chromatography on a silica column, gas chromatography, extraction, filtration and passage through charcoal or resin, separated, where appropriate, in pure form or in the form of a mixture, into their possible optical isomers, or salified with a pharmaceutically acceptable acid or base.

The compounds of formula (II/e) as defined above are also readily accessible to a person skilled in the art by reacting a compound of formula (II/a):

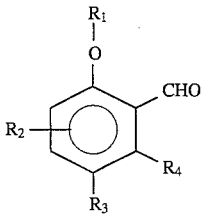 (II/a)

in which $R_1$, $R_2$, $R_3$, and $R_4$ are as defined in the formula (I), with nitromethane in order to obtain a compound of formula (II/f):

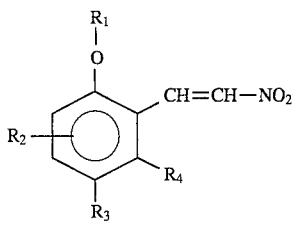 (II/f)

in which $R_1$, $R_2$, $R_3$, and $R_4$ are as defined above, which is then reduced to obtain the corresponding compound of formula (II/e).

The compounds of formula (II) in which A represents an ethylene moiety substituted with a lower alkyl may be obtained by a person skilled in the art by reacting a compound of formula (II/a):

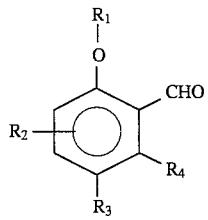 (II/a)

in which $R_1$, $R_2$, $R_3$, and $R_4$ are as defined in the formula (I), with a nitro compound of formula (II/g):

A'—$NO_2$ (II/g)

in which A' represents a methyl group substituted with a lower alkyl, in order to obtain a compound of formula (II/f'):

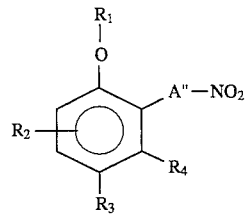 (II/f')

in which $R_1$, $R_2$, $R_3$, and $R_4$ are as defined above and A" represents an ethylene moiety substituted with a lower alkyl, which compound of formula (II/f') is subjected to a reduction step and, where appropriate, alkylated by reaction with a compound of formula (V):

Hal'''—$R_5$' (V)

in which $R_5$, represents a linear or branched alkyl having 1 to 6 carbon atoms and Hal''' represents a halogen atom, in order to obtain the corresponding compound of formula (II).

The Applicant discovered that the compounds of the invention possessed noteworthy activity with respect to the melatoninergic system. They exhibit, in particular, a very high affinity for melatonin receptors.

This very considerable binding capacity is demonstrated in Example B (study of binding to melatonin receptors) of the present application.

The intensity of this pharmacological property of the compounds of the invention proved surprising, since it is not encountered with compounds in which the hydroxyl or alkoxy group is a substituent at the meta or para position of the benzene ring carrying the alkylamide chain.

By virtue of their action on melatonin receptors, the compounds of the invention are hence new candidates for the treatment of disorders of the melatoninergic system.

Pathologies in which melatonin is involved are, in particular, sleep disorders, depression, Parkinson's disease, Alzheimer's disease, cancer, jet lag, immune disorders, migraine, diabetes and stress. Melatonin is also implicated in a mechanism of inhibition of ovulation.

The invention also encompasses pharmaceutical compositions containing as active principle at least one of the compounds of formula (I) or one of its addition salts with a pharmaceutically acceptable acid or base, in combination with one or more pharmaceutically acceptable excipients.

Among the compositions according to the invention, there may be mentioned, as examples and without implying any limitation, those which are suitable for oral, parenteral, ocular, per- or transcutaneous, nasal, rectal, perlingual or respiratory administration, and in particular injections, aerosols, eye or nose drops, tablets, sublingual tablets, capsules including hard gelatin capsules, troches, preparations to be held under the tongue, suppositories, creams, ointments and gels.

The preparations thereby obtained generally take the form of individual measured doses, and can contain, depending on the pathologies being treated and the patient's age and sex, from 0.01 to 100 mg in doses taken from one to three times a day, and more especially from 0.1 to 10 mg, for example from 0.1 to 10 mg.

The examples which follow illustrate the invention and in no way limit it. The structure of the compounds is verified by nuclear magnetic resonance.

PREPARATION 1:
2-(2-METHOXY-1-NAPHTHYL)ETHYLAMINE

First method:

STAGE A:
(2-METHOXY-1-NAPHTHYL)METHANOL 40 cm$^3$ of anhydrous tetrahydrofuran (THF) are placed under argon in a 250-cm$^3$ two-necked flask. 3.1 g of lithium aluminum hydride are added. A solution of 5 g of (2-methoxy-1-naphthyl)carbaldehyde in 30 cm$^3$ of anhydrous tetrahydrofuran is added to this mixture with stirring. Reaction is allowed to proceed at room temperature for 16 h. Hydrolysis is performed according to the following method:

- 3.1 cm$^3$ of water are added to the mixture, which is left stirring for 5 min,
- 3.1 cm$^3$ of 15% sodium hydroxide solution are then added, and the mixture is left stirring again for 5 minutes,
- 9.3 cm$^3$ of water are then added until a whitish pasty mixture is obtained.

After incorporation of sodium sulfate and stirring for a further few minutes, the mixture is filtered and the filtrate is concentrated in a rotary evaporator.

White crystals of the desired alcohol, representing a mass of 4.87 g, are thereby obtained. (Yield: 96%).

The compound is recrystallized in the heated state in an isopropyl ether/ethanol mixture to give 3.65 g of white crystals of (2-methoxy-1-naphthyl)methanol.

Melting point: 100.9°±0.2° C.
$^1$H NMR (CDCl$_3$, 200 MHz)
2.01 ppm (1H (OH), b.s.)
3.90 ppm (3H (CH$_3$O), s.)
5.10 ppm (2H (CH$_2$O), s.)
7.17–8.06 ppm (6H (aromatic), m.)

STAGE B: 1-CHLOROMETHYL-2-METHOXYNAPHTHALENE 2.21 g of the compound obtained in Stage A are placed in a 100-cm$^3$ two-necked flask. The flask is placed under argon. 17.6 cm$^3$ of toluene (1.5 equivalents) are incorporated, followed by 0.94 cm$^3$ of pyridine (1 equivalent). The flask is immersed in an ice bath. A solution of 2 cm$^3$ of thionyl chloride in 12 cm$^3$ of toluene is then added via a pressure-equalizing dropping funnel. A white precipitate forms. After the addition, the ice bath is removed. Reaction is allowed to proceed at room temperature for 15 h.

This mixture is poured into ice; the reaction medium is left stirring for 45 min. After separation of the aqueous and organic phases, the latter is washed once with water, once with saturated sodium hydrogen carbonate solution and then once with saturated sodium chloride solution. After drying over magnesium sulfate and concentration of the filtrate, a yellow crystalline product of mass 2.24 g, corresponding to 1-chloromethyl-2-methoxynaphthalene, is isolated. (Yield: 92.3%).

These crystals may be recrystallized in the heated state in ethyl ether; 1-chloromethyl-2-methoxynaphthalene is a crystalline white solid.

Melting point: 122.7°±0.2° C.
$^1$H NMR (CDCl$_3$, 200 MHz)
3.92 ppm (3H (OCH$_3$), s.)
5.10 ppm (2H (CH$_2$Cl), s.)
7.18 ppm (1H (atom.), s. J=8.9 Hz)
7.27–7.34 ppm (1H (aromatic), m.)
7.45–7.53 ppm (1H (aromatic), m.)
7.73 ppm (1H (aromatic), d. J=8.9 Hz)
7.77 ppm (1H (aromatic), d. J=8.9 Hz)
7.96 ppm (1H (aromatic), d. J=8.9 Hz)

STAGE C:
1-CYANOMETHYL-2-METHOXYNAPHTHALENE

The reaction involves 1.14 g of the compound obtained in Stage B, 0.718 g of potassium cyanide (2 equivalents) and a small spatula of potassium iodide, these reactants being present in 12 cm$^3$ of anhydrous dimethyl sulfoxide (2 equivalents). It is carried out under argon at 120°–140° C., and lasts 8 h. Treatment after the reaction yields rust-colored crystals, which are recrystallized in the heated state in a hexane/ethyl acetate mixture.

0.665 g of beige crystals of 1-cyanomethyl-2-methoxynaphthalene is thereby isolated. (Yield: 61%).

Melting point: 95.4°±0.2° C.
$^1$H NMR (CDCl$_3$, 200 MHz)
3.94 ppm (3H (CH$_3$O), s.)
4.05 ppm (2H (CH$_2$CN), s.)
7.18–7.83 ppm (6H (aromatic), m.)

STAGE D:
2-(2-METHOXY-1-NAPHTHYL)ETHYLAMINE

The reaction is performed on 0.6 g of the compound obtained in the preceding stage (3 mmol), in 10 cm$^3$ of absolute ethanol (3 equivalents) and 1 cm$^3$ of ammonium hydroxide.

The compound is hydrogenated at atmospheric pressure and at room temperature on Raney nickel. Reaction is allowed to proceed for 23 hours. The catalyst is removed by filtration on a layer of Celite and rinsed with absolute ethanol. The filtrate is concentrated in a rotary evaporator. The amine hydrochloride is then formed: the mixture is diluted in methanol, methanolic hydrogen chloride is added and the hydrochloride is precipitated by adding isopropyl ether.

0.468 g of yellow crystals of 2-(2-methoxy-1-naphthyl) ethylamine hydrochloride is thereby isolated. (Yield: 64.5%)

Melting point: >180° C.

$^1$H NMR (CD$_3$OD, 200 MHz)

3.30–3.37 ppm (2H (CH$_2$—), m.)

3.62–3.69 ppm (2H (CH$_2$N), m.)

4.19 ppm (3H (CH$_3$O), s.)

7.55–7.76 ppm (3H (aromasic), m.)

8.01–8.20 ppm (3H (aromatic), m.)

Second method:

STAGE A': 1-NITRO-2-(2-METHOXY-1-NAPHTHYL)ETHYLENE 1.52 g of 2-methoxynaphthaldehyde (8.16 mmol), 0.4 g of ammonium acetate (5.19 mmol) and 20 cm$^3$ of nitromethane (96%) are introduced into a 50-cm$^3$ two-necked round-bottomed flask equipped with a condenser. The reaction mixture is heated to reflux for 1 h 30 min while stirring. It becomes yellow. The nitromethane is evaporated off in a rotary evaporator and the residue is then taken up with dichloromethane. Hydrolysis of the ammonium acetate is carried out by pouring the above mixture into water. The aqueous phase is washed twice with CH$_2$Cl$_2$, the organic phase once with water. The latter phase is dried with MgSO$_4$ and the solvent is removed in a rotary evaporator. 1.77 g of yellow crystals (equivalent to 7.73 mmol of the expected product) are then obtained, corresponding to a 95% yield.

Melting point: 138.6°±0.4° C.

$^1$H NMR (CDCl$_3$, 200 MHz)

4.04 ppm (3H (MeO), s)

8.82–8.76 ppm (1H(CHNO$_2$), d, J=13.35 H$_3$)

8.13–8.06 ppm (1H (naph-CH), d, J=13.42 H$_3$)

7.23–8.14 ppm (6H (arom), multiplier consisting of 2 doublets of triplets: 7.60–7.56–7.52 ppm, J=7.15 Hz, 7.41–7.37–7.34 ppm J=7.2 Hz, and of 4 doublets: 8.14–8.09 ppm J=8.55 Hz, 7.94–7.90 ppm J=9.18 Hz, 7.78–7.74 ppm J=8 HZ, 7.28–7.23 ppm J=9.7 Hz)

Thin-layer chromatography:

Rf=0.93 (CH$_2$Cl$_2$)

STAGE B': 2-(2-METHOXYNAPHTHYL)ETHYLAMINE

Under an inert atmosphere, 50 cm$^3$ of anhydrous THF are introduced into a 250-cm$^3$ three-necked round-bottomed flask equipped with a condenser and a 100-cm$^3$ dropping funnel, and 1.74 g (45.82 mmol) of LiAlH$_4$ are then introduced while cooling the flask in ice and stirring the reaction medium. Under the same conditions, a mixture consisting of 2.05 g (8.94 mmol) of compound obtained in the preceding stage and 75 cm$^3$ of THF are then added in the course of 1 h. After the introduction of reactants, the mixture is heated for approximately 24 h to a temperature of between 30 and 40° C. Hydrolysis of the excess hydride is performed by cooling the flask again with ice and adding 1.6 cm$^3$ of water, 1.6 cm$^3$ of 15% NaOH, 37 cm$^3$ of ether and 4.7 cm$^3$ of water.

After filtration, the mixture is dried with anhydrous sodium carbonate, concentrated in a rotary evaporator and purified by chromatography on a silica column (eluents: ethyl acetate, Rf=0, then a mixture consisting of 15% of methanol, 10% of triethylamine and 75% of ethyl acetate, Rf =0.28). 1.42 g (7.06 mmol) of 2-(2-methoxynaphthyl)ethylamine (orange-yellow viscous oil) are finally obtained, equivalent to a yield after purification of 78.9%.

PREPARATIONS 2 TO 7:

Using the procedure described in Preparation 1, but replacing (2-methoxy-1-naphthyl)carbaldehyde in Stage A by:

(2,5,6-trimethoxy-1-naphthyl)carbaldehyde (Eur. J. Med. Chem. 1980, 19 (3) pp 249–253), PREPARATION 2: 2-(2,5,6-TRIMETHOXY-1-NAPHTHYL)ETHYLAMINE is obtained 6-hydroxy-2-methoxy-1-naphthyl)carbaldehyde (Eur. J. Med. Chem. 1983, 18 (2), pp 169–174), PREPARATION 3: 2-(6-HYDROXY-2-METHOXY-1-NAPHTHYL)ETHYLAMINE is obtained (2,6-dipropoxy-1-naphthyl)carbaldehyde (J. Org. Chem. 1981, 46 (9), pp 1832–1835), PREPARATION 4: 2-(2,6-DIPROPOXY-1-NAPHTHYL)ETHYLAMINE is obtained (5,6,7,8-tetrahydro-4-methyl-2-methoxy-1-naphthyl)carbaldehyde (Aust. J. Chem. 1981, 34 (2), pp 459–464), PREPARATION 5: 2-(5,6,7,8-TETRAHYDRO-4-METHYL-2-METHOXY-1-NAPHTHYL)ETHYLAMINE is obtained 5-formyl-6-methoxy-1,4-benzodioxane (J. Heterocycl. Chem. 1989, 26 (1), pp 193–197), PREPARATION 6: 2-(6-METHOXY-1,4-BENZODIOXAN-5-YL)ETHYLAMINE is obtained 7-formyl-6-methoxy-3-methylbenzofuran (Bull. Soc. Chim. Fr. 1975, 11–12, Pt. 2, pp 2763–2766), PREPARATION 7: 2-(6-METHOXY-3-METHYLBENZOFURAN-7-YL)ETHYLAMINE is obtained.

PREPARATION 8: 2-(5-BROMO-2-METHOXYPHENYL)ETHYLAMINE

STAGE A: (5-BROMO-2-METHOXYPHENYL)METHANOL 30 cm$^3$ of anhydrous tetrahydrofuran are placed in a 250-cm$^3$ two-necked flask. The flask is chilled and 2.66 g of lithium aluminum hydride are added. 5.014 g of 5-bromo-2-methoxybenzaldehyde dissolved in 30 cm$^3$ of anhydrous tetrahydrofuran are added via a pressure-equalizing dropping funnel (the assembly is under an argon atmosphere). The dropping funnel is then rinsed with 10 cm$^3$ of anhydrous tetrahydrofuran and the mixture is left stirring vigorously at room temperature for 5 h. Hydrolysis is carried out as follows:

addition of 2.7 cm$^3$ of water, stirring of this mixture for 5 min, addition of 2.7 cm$^3$ of 15% sodium hydroxide solution, stirring for 5 min, then addition of 3 times 2.7 cm$^3$ of water until a white mass is obtained.

Sodium sulfate is then incorporated in order to dry the mixture.

After filtration and concentration of the filtrate, a white solid weighing 4.4 g is obtained, analysis of which shows it to be the desired alcohol.

$^1$H NMR (CDCl$_3$, 200 MHz)

2.38 ppm (1H (OH), b.s.)

3.75 ppm (3H (CH$_3$O), s.)

4.55 ppm (2H (CH$_2$O), b.s.)

6.66 ppm (1H (aromatic), d. J=8.6 Hz)

7.17–7.34 ppm (2 H (aromatic), m.)

STAGE B: 5-BROMO-2-METHOXYBENZYL CHLORIDE 4.023 g of the compound obtained in Stage A are placed in a 100-cm$^3$ two-necked flask. The compound is dissolved in 28 cm$^3$ of anhydrous toluene. The mixture is placed under argon. 1.5 cm$^3$ of pyridine are introduced with a syringe.

To this mixture which is stirred and chilled, 3.2 cm$^3$ of thionyl chloride diluted in 18 cm$^3$ of anhydrous toluene are added via a pressure-equalizing dropping funnel. After the addition, the ice bath is removed. Reaction is allowed to proceed at room temperature for 18 h. The mixture is hydrolyzed by pouring it into ice. The resulting mixture is left stirring vigorously for 45 min. The organic and aqueous phases are separated. The organic phase is washed with water, then with saturated aqueous sodium hydrogen carbonate solution and with saturated aqueous sodium chloride solution. After drying over magnesium sulfate and concentration of the filtrate, an orange liquid is isolated and chromatographed on silica (eluent: ether/pentane, 20:80–40:60). A colorless liquid of mass 4.17 g, which crystallizes in the cold state, is thereby collected.

$^1$H NMR (CDCl$_3$, 200 MHz)

3.78 ppm (3H (CH$_3$O), s.)

4.51 ppm (2H (CH$_2$Cl), s.)

6.69 ppm (1H (aromatic), d. J=8.6 Hz)

7.24–7.41 ppm (2H (atom.), m.)

STAGE C: 5-BROMO-1-CYANOMETHYL-2-METHOXYBENZENE 2.23 g of potassium cyanide and a small spatula of potassium iodide in 35 cm$^3$ of anhydrous dimethyl sulfoxide are added to 4.03 g of the compound obtained above.

This mixture under argon is brought to 120°–140° C. for 5 h.

Treatment after the reaction yields a rust-colored liquid which is chromatographed on silica (eluent: ether/pentane: 30:70–100:0).

In order to obtain the pure compound, the first fraction is recrystallized in the heated state in a hexane/ethyl acetate mixture.

1.35 g of yellow crystals of 5-bromo-1-cyanomethyl-2methoxybenzene are thereby isolated, analysis of which confirms the purity.

Melting point: 60.7°±0.2° C.

$^1$H NMR (CDCl$_3$, 200 MHz)

3.58 ppm (2H (CH$_2$CN), s.)

3.78 ppm (3H (CH$_3$O), s.)

6.70 ppm (1H (aromatic), d. J=8.7 Hz)

7.34 ppm (1H (aromatic), d.d. J=2.3 Hz, J=8.7 Hz)

STAGE D: 2-(5-BROMO-2-METHOXYPHENYL)ETHYLAMINE

Using the procedure described in Stage D of Preparation 1, but replacing 1-cyanomethyl-2-methoxynaphthalene by 5-bromo-1-cyanomethyl-2-methoxybenzene obtained in the preceding stage, 2-(5-bromo-2-methoxyphenyl)ethylamine is obtained.

PREPARATION 9: 1-METHYL-2-(2-METHOXY-1-NAPHTHYL)ETHYLAMINE

STAGE A: 2-NITRO-1-(2-METHOXY-1-NAPHTHYL)PROPENE 2.13 g (11.20×10$^{-3}$ mol) of naphthaldehyde, 30 cm$^3$ of nitroethane and 0.54 g (7×10$^{-3}$ mol) of ammonium acetate are introduced into a round-bottomed flask. The mixture is stirred and heated to reflux for 2 hours. The nitroethane is then evaporated off under reduced pressure, the residue is taken up with CH$_2$Cl$_2$ and water is added to hydrolyze the acetate. After separation of the two phases, the organic phase is washed with water, the aqueous phases with CH$_2$Cl$_2$ (twice). The organic phase is then dried over MgSO$_4$ and concentrated under reduced pressure. 2.59 g (10.64×10$^{-3}$ mol) of the expected nitroethylenic compound (yellow solid) are then contained, equivalent to a 95% yield.

Melting point: 72°±3° C.

$^1$H NMR (200 MHz, CDCl$_3$) δ (ppm):

Z compound: 2.1 (s, 3H, CH$_3$); 3.97 (s, 3H, MeO); 7.23/7.96 (n, 6H, aromatic); 8.33 (s, 1H, ethylenic H) (68%)

E compound: 2.52 (s, 3H, CH$_3$); 3.89 (s, 3H, MeO); 6.92 (s, 1H, ethylenic H); 7.23/7.96 (n, 6H, aromatic) (32%)

STAGE B: 1-METHYL-2-(2-METHOXY-1-NAPHTHYL)ETHYLAMINE 50 cm$^3$ of anhydrous THF are introduced into a 250-cm$^3$ three-necked flask under an inert atmosphere, the solvent is stirred and the flask is cooled with ice. 1.45 g (38.19×10$^{-3}$ mol) of LiAlH$_4$ are introduced in small portions, and a mixture consisting of 60 cm$^3$ of anhydrous THF and 2.09 g (8.59×10$^{-3}$ mol) of the nitroethylenic compound is then introduced dropwise. The ice bath is then removed, and after the mixture is returned to room temperature, it is heated to 40° C. for 24 h. Hydrolysis of the excess hydride is carried out as follows: the mixture is cooled with ice, and 1.5 cm$^3$ of water, 1.5 cm$^3$ of 15% sodium hydroxide, 30 cm$^3$ of ether and 4.5 cm$^3$ of water are added. The mixture is filtered and the filtrate is then dried over MgSO$_4$ and evaporated to dryness. The residue obtained is purified by chromatography on a silica column (eluent: ethyl acetate, then 15:3:2 ethyl acetate/methanol/triethylamine mixture). 1.09 g (5.06×10$^{-3}$ mol) of the expected amine are finally isolated, equivalent to a 59% yield.

PREPARATION 10: 2-(2-METHOXY-5-METHYLPHENYL)ETHYLAMINE

STAGE A: METHYL 2-METHOXY-5-METHYLBENZOATE 5.07 g (33.32×10$^{-3}$ mol) of 5-methylsalicylic acid and 22.33 g (161.6×10$^{-3}$ mol) of annydrous potassium carbonate are introduced into a 250-cm$^3$ two-necked flask. 175 cm$^3$ of anhydrous acetone are added under an inert atmosphere. The reaction mixture is stirred, 7.25 cm$^3$ (76.62×10$^{-3}$ mol) of dimethyl sulfate are added with a syringe and the mixture is brought to reflux for 6 h. Hydrolysis of the dimethyl sulfate is performed by adding 5 cm$^3$ of water. After filtration and evaporation of the solvent, the residue is taken up with dichloromethane, dried over MgSO$_4$ and then evaporated to dryness. The crude product is purified by chromatography on a silica column (eluent: $CH_2Cl_2$) to give 5.47 g (30.36× $10^{-3}$ mol) of the expected ester, equivalent to a 91% yield.

Boiling point (12 mmHg): 128°–132° C.

STAGE B: (2-METHOXY-5-METHYLPHENYL)METHANOL 1.56 g (41.08×$10^{-3}$ mol) of $LiAlH_4$ are introduced into a 500-$cm^3$ three-necked flask containing 100 $cm^3$ of anhydrous THF and under an inert atmosphere, while cooling the flask with an ice bath. A mixture consisting of 4.99 g (27.69×$10^{-3}$ mol) of the above ester and 150 $cm^3$ of anhydrous THF is then introduced dropwise in the course of 1 hour, the flask being maintained at 0° C.

After it has returned to room temperature, the reaction mixture is heated to reflux for 20 h. Hydrolysis of the excess hydride is performed by cooling the flask with ice and adding slowly 1.3 $cm^3$ of water, then 1.3 $cm^3$ of 15% sodium hydroxide, 40 $cm^3$ of ether and 5 $cm^3$ of water. After filtration, drying of the filtrate with $MgSO_4$ and evaporation thereof to dryness, the residue is purified by vacuum distillation to give 3.68 g (24.18×$10^{-3}$ mol) of the expected alcohol, equivalent to an 87% yield.

Boiling point (12 mmHg): 130°–132° C.

STAGE C: 2-METHOXY-5-METHYLBENZYL CHLORIDE 3.23 g (21.22×$10^{-3}$ mol) of benzyl alcohol and 50 $cm^3$ of anhydrous toluene are introduced into a 100-$cm^3$ three-necked flask. Under argon, while stirring and cooling the reaction mixture, 1.70 $cm^3$ (21.10×$10^{-3}$ mol) of pyridine dried over potassium hydroxide are introduced, followed by 3.5 $cm^3$ (47.98×$10^{-3}$ mol) of thionyl chloride. A white precipitate forms and hydrogen chloride is evolved. After introduction of the reactants, reaction is allowed to proceed at room temperature for approximately 24 h. The mixture is then poured into an ice bath and stirred for 1 h. The organic phase is recovered, washed with water, saturated sodium bicarbonate solution and saturated sodium chloride solution and lastly dried over $MgSO_4$. After evaporation to dryness, the residue is purified by vacuum distillation and 2.5 g (14.65×$10^{-3}$ mol) of the expected chloride are obtained, equivalent to a 69% yield.

Boiling point (13 mmHg): 117°–120° C.

STAGE D: 1-CYANOMETHYL-2-METHOXY-5-METHYLBENZENE 2.44 g (14.30×$10^{-3}$ mol) of the benzyl chloride obtained in the preceding stage and 50 $cm^3$ of dimethyl sulfoxide (DMSO) are introduced into a 250-$cm^3$ three-necked flask. The mixture is stirred and, under an inert atmosphere, a spatula of potassium iodide and 1.85 g (28.41×$10^{-3}$ mol) of potassium cyanide are added. Reaction is allowed to proceed at room temperature for 20 h. After evaporation of the DMSO under vacuum, the residue is taken up with $CH_2Cl_2$ and the KCN and KI are hydrolyzed by adding water. The aqueous phase is washed with dichloromethane, and the combined organic phases with water. The latter phases are then dried over $MgSO_4$ and evaporated to dryness. The crude product obtained is purified by distillation under reduced pressure, and 2.11 g (13.09×$10^{-3}$ mol) of the expected nitrile are obtained, equivalent to a 91% yield.

Boiling point (16 mmHg)=136°–140° C.

STAGE E: 2-(2-METHOXY-5-METHYLPHENYL)ETHYLAMINE 1.7 g (0.54×$10^{-3}$ mol) of nitrite 38 $cm^3$ of 95.96% ethanol and 3.8 $cm^3$ of ammonia solution are introduced into a 100-$cm^3$ three-necked flask. Under an inert atmosphere, a spatula-tip of Raney nickel is introduced. After the whole of the assembly has been placed under vacuum, a hydrogen atmosphere is established therein and the reaction medium is stirred vigorously. It is then heated to 40°–50° C. for approximately 48 h. After cooling, the mixture is filtered through Celite and the latter is washed with ethanol. The filtrate is evaporated to dryness, the residue is taken up with ether and the mixture is evaporated again. The crude product obtained is purified by converting the amine obtained to the hydrochloride. A greenish-yellow solid product is obtained, which has to be recrystallized in an ethanol/ether mixture. 1.07 g (5.31×$10^{-3}$ mol) of white hydrochloride are then obtained.

Melting point: 170°±3° C.

Elemental analysis:

| | |
|---|---|
| C theo = 59.55% | C exp = 39.39% |
| H theo = 7.99% | H exp = 7.85% |
| N theo = 6.94% | H exp = 6.78% |
| Cl theo = 17.58% | Cl exp = 17.54% |

PREPARATION 11: 2-(5-ETHYL-2-METHOXYPHENYL)ETHYLAMINE

20 $cm^3$ of anhydrous THF are introduced into a 50-$cm^3$ three-necked flask under an inert atmosphere, and the solvent is stirred and cooled with ice. 0.43 g (11.32×$10^{-3}$ mol) of $LiAlH_4$ is then introduced in small portions. 0.51 g (2.45×$10^{-3}$ mol) of 1-nitro-2-(5-ethyl-2-methoxyphenyl)ethylene, prepared according to synthesis methods known to a person skilled in the art, is then introduced dropwise.

After the introduction, the reaction medium is heated to 40° C. for 18 h. After cooling, the excess hydride is hydrolyzed by adding 0.5 $cm^3$ of water, 0.5 $cm^3$ of 15% NaOH, 15 $cm^3$ of ether and 1.5 $cm^3$ of water to the mixture cooled with ice. After filtration, the filtrate is dried over $MgSO_4$ and evaporated to dryness, and the residue is purified by chromatography on a silica column (eluent: ethyl acetate, then ethyl acetate/MeOH/$Et_3N$, 15:3:2). The amine obtained is solubilized in $CH_2Cl_2$, and 2 equivalents (eq.) of ethereal hydrogen chloride are Then added. After evaporation of the solvents, a beige precipitate is obtained, which has to be recrystallized in an ethanol/ether mixture. 150 mg (6.95×$10^{-3}$ mol) are finally obtained, equivalent to a final yield of 28% of the hydrochloride of the expected amine.

Melting point: 173°±3° C.

EXAMPLE 1: N-[2-(2-METHOXY-1-NAPHTHYL)ETHYL]ACETAMIDE 0.3 g (1.2 mmol) of 2-(2-methoxy-1-naphthyl)ethylamine hydrochloride (Preparation 1) is placed in a 50-$cm^3$ two-necked flask. 10 $cm^3$ of distilled water are added until the crystals have dissolved, followed by 0.1 g of sodium acetate (13 equivalents). 3 $cm^3$ of acetic anhydride (25 equivalents) are added to this mixture with stirring. The solution becomes milky, a slight evolution of heat takes place and the solution then becomes clear. After 25 min of reaction the mixture is extracted with dichloromethane. The organic phases are washed with saturated aqueous sodium hydrogen carbonate solution and then with water and dried over magnesium sulfate. The concentrated filtrate gives pale yellow crystals, which are recrystallized directly in the heated state in a hexane/ethyl acetate mixture.

0.235 g of white crystals of N-[2-(2-methoxy-1-naphthyl)ethyl]acetamide is thereby obtained.

Yield: 76.8%

Melting point: 138.7° C.

$^1$H NMR (CDCl$_3$, 200 MHz)

3.22–3.29 ppm (2H (CH$_2$N), m.)

3.43–3.52 ppm (2H (CH$_2$O), m.)

3.90 ppm (3H (CH$_3$O), s.)

5.69 ppm (1H (NH), b.s.)

7.19–7.31 ppm (2H (aromatic), m.)

7.39–7.47 ppm (1H (aromatic), m.)

7.68–7.74 ppm (2H (aromatic), m.)

7.94 ppm (1H (atom.), d. J=8.6 Hz)

EXAMPLE 2: N-[2-(2-METHOXY-1-NAPHTHYL)ETHYL]PROPIONAMIDE

First method:

0.22 g of 2-(2-methoxy-1-naphthylethylamine) is placed in a 25-cm$^3$ two-necked flask. The compound is diluted with 5.3 cm$^3$ of anhydrous dichloromethane (3 equivalents). After the mixture has been placed under argon and the flask has been chilled, 0.250 cm$^3$ of triethylamine is added to the mixture, followed by 0.160 cm$^3$ of propanoyl chloride added slowly (1 equivalent each). After 30 min of reaction at room temperature, subsequent treatment yields a brown liquid which is chromatographed on a silica column (eluent: CH$_2$Cl$_2$/ methane, 0.2%). The product isolated crystallizes at room temperature. It is recrystallized by dissolution in the heated state in a hexane/ethyl acetate mixture.

0.193 g of beige crystals of N-[2-(2-methoxy-1-naphthyl)ethyl]propionamide is thereby obtained.

Melting point: 100.2°±0.2° C.

$^1$H NMR (CDCl$_3$, 200 MHz)

1.01 ppm (3H (CH$_3$), t. J=7.6 Hz)

2.05 ppm (2H (CH$_2$), q. J=7.6 Hz)

3.23–3.29 ppm (2H (CH$_2$), m.)

3.44–3.54 ppm (2H (CH$_2$N), m.)

3.90 ppm (3H (CH$_3$O), s.)

5.70 ppm (1H (NH), b.s.)

7.24–7.47 ppm (3H (aromatic), m.)

7.68–7.73 ppm (2H (aromatic), m.)

7.95 ppm (1H (atom.), d. J=8.6 Hz)

Elemental analysis (C$_{16}$H$_{19}$NO$_2$)

|   | calculated | found |
|---|---|---|
| C | 74.68% | 74.15% |
| H | 7.44% | 7.38% |
| N | 5.44% | 5.26% |

Second method:

1.40 g (6.96 mmol) of 2-(2-methoxynaphthyl)ethylamine, which is solubilized in 20 cm$^3$ of anhydrous dichloromethane, are introduced into a 100-cm$^3$ two-necked flask under an inert atmosphere. The mixture is cooled with an ice bath and stirred, and 1.5 cm$^3$ (10.4 mmol) of triethylamine dried over potassium hydroxide and 0.7 cm$^3$ (8.056 mmol) of propanoyl chloride are introduced. After the introduction of the reactants, the ice bath is removed and reaction is allowed to proceed at room temperature for 30 min. Hydrolysis of the excess chloride is carried out by pouring the reaction mixture into water. After extraction three times with dichloromethane, the organic phase is dried over magnesium sulfate. After evaporation of the solvent and recrystallization of the solid obtained, in the heated state, in a pentane/ethyl acetate mixture, 0.70 g (2.72 mmol) of N-[2-(2-methoxy-1-naphthyl)ethyl]propionamide (white solid) is obtained, equivalent to a yield after purification of 39%.

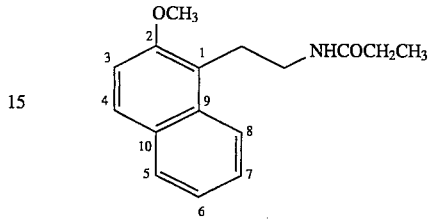

EXAMPLE 3: N-[2-(2-METHOXY-1-NAPHTHYL)ETHYL] CYCLOPROPYLCARBOXAMIDE

Using the procedure described in Example 2, but with cyclopropanecarbonyl chloride instead of propanoyl chloride, the compound of the title is obtained:

Melting point: 127.5±0.2° C.

$^1$H NMR (CDCl$_3$, 200 MHz)

0.56–0.65 ppm (2H (CH$_2$ (cyclopropyl)), m.)

0.85–0.92 ppm (2H (CH$_2$ (cyclopropyl)), m.)

1.08–1.18 ppm (1H (CH (cyclopropyl)), m.)

3.23–3.30 ppm (2H (CH$_2$) m.)

3.44–3.54 ppm (2H (CH$_2$N) m.)

3.90 ppm (3H(CH$_3$—O), s.)

5.86 ppm (1H(NH), b.s.)

EXAMPLE 4: N-[2-(2-METHOXY-1-NAPHTHYL)ETHYL]TRIFLUOROACETAMIDE 0.338 g of 2-(2-methoxy-1-naphthyl)ethylamine is placed in a 25-cm$^3$ two-necked flask. It is diluted with 5 cm$^3$ of anhydrous dichloromethane (3 equivalents). After the flask has been placed under argon, 0.15 cm$^3$ of pyridine stored over potassium hydroxide (1.1 equivalents) is added, the flask is chilled and 0.24 cm$^3$ of trifluoroacetic anhydride (1 equivalent) is added slowly. The reaction lasts 30 minutes at room temperature. Treatment after the reaction yields 0.220 g of viscous yellow liquid which crystallizes at room temperature. It is recrystallized by dissolution in the heated state in a hexane/ethyl acetate mixture.

52 mg of white crystals corresponding to the compound of the title are thereby obtained:

Melting point: 87.4°±0.2° C.

$^1$H NMR (CDCl$_3$, 200 MHz)

3.30–3.37 ppm (2H (CH$_2$), m.)

3.55–3.64 ppm (2H (CH$_2$N), m.)

3.91 ppm (3H (CH$_3$O), s.)

6.97 ppm (1H (NH), b.s.)

7.18–7.49 ppm (3H (atom.), m.)

7.72–7.87 ppm (3H (atom.), m.)

$^{19}$F NMR (CDCl$_3$, 188.3 MHz)

75.99 ppm (CF$_3$, s.)

EXAMPLE 5: N-[2-(2-METHOXYNAPHTHYL)ETHYL]BUTYRAMIDE

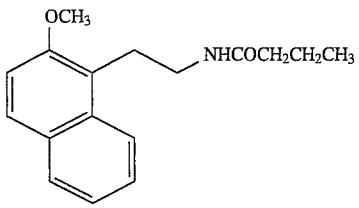

EXEMPLE 5

0.45 g (2.23 mmol) of 2-(2-methoxy-1-naphthyl)ethylamine, which is solubilized in 20 cm³ of anhydrous dichloromethane, is introduced into a 100-cm³ two-necked flask under an inert atmosphere. The mixture is cooled with an ice bath and stirred, and 0.47 cm³ (3.37 mmol) of triethylamine dried over potassium hydroxide is introduced, followed by 0.28 cm³ (2.69 mmol) of butyryl chloride. After the introduction of the reactants, the ice bath is removed and reaction is allowed to proceed at room temperature for 30 min. Hydrolysis of the excess chloride is carried out by pouring the reaction mixture into water. After extraction three times with dichloromethane, the organic phase is dried over magnesium sulfate. After evaporation of the solvent and recrystallization of the solid obtained, in the heated state, in a pentane/ethyl acetate mixture, 0.29 g (1.07 mmol) of N-[2-(2-methoxynaphthyl)ethyl]butyramide (white solid) is obtained, equivalent to a yield after purification of 48%.

Melting point: 76°±3° C.

Elemental analysis:

| C theo = 75.24% | C exp = 75.14% |
|---|---|
| H theo = 7.80% | H exp = 7.84% |
| N theo = 5.16% | N exp = 5.16% |

EXAMPLE 6: N-[2-(2-METHOXY-1-NAPHTHYL)ETHYL]PENTANAMIDE 0.59 g (2.93 mmol) of 2-(2-methoxy-1-naphthyl)ethylamine, which is solubilized in 20 cm³ of anhydrous dichloromethane, is introduced into a 100-cm³ two-necked flask under an inert atmosphere. The mixture is cooled with an ice bath and stirred, and 0.61 cm³ (4.37 mmol) of triethylamine dried over potassium hydroxide is introduced, followed by 0.42 cm³ (3.54 mmol) of valeryl chloride. After the introduction of the reactants, the ice bath is removed and reaction is allowed to proceed at room temperature for 30 min. Hydrolysis of the excess chloride is carried out by pouring the reaction mixture into water. After extraction three times with dichloromethane, the organic phase is dried over magnesium sulfate. After evaporation of the solvent and recrystallization of the solid obtained, in the heated state, in a pentane/ethyl acetate mixture, 0.39 g (1.37 mmol) of N-[2-(2-methoxynaphthyl)ethyl]pentanamide (white solid) is obtained, equivalent to a yield after purification of 47%.

Melting point: 72°±3° C.

EXAMPLES 7 TO 12:

Using the procedure described in Example 2, but replacing propanoyl chloride by the appropriate acid chloride, the compounds of the following examples are obtained:
EXAMPLE 7: N-[2-(2-METHOXY-1-NAPHTHYL)ETHYL]HEXANAMIDE
EXAMPLE 8: N-[2-(2-METHOXY-1-NAPHTHYL)ETHYL]HEPTANAMIDE
EXAMPLE 9: N-[2-(2-METHOXY-1-NAPHTHYL)ETHYL]CROTONAMIDE
EXAMPLE 10: N-[2-(2-METHOXY-1-NAPHTHYL)ETHYL]CYCLOBUTYLCARBOXAMIDE
EXAMPLE 11: N-[2-(2-METHOXY-1-NAPHTHYL)ETHYL]-4-CHLOROBUTYRAMIDE
EXAMPLE 12: N-[2-(2-METHOXY-1-NAPHTHYL)ETHYL]CYCLOHEXYLCARBOXAMIDE
EXAMPLE 13: N-[2-(2,5,6-TRIMETHOXY-1-NAPHTHYL)ETHYL]ACETAMIDE Using the procedure described in Example 1, but replacing 2-(2-methoxy-1-naphthyl)ethylamine by 2-(2,5,6trimethoxy-1-naphthyl)ethylamine (Preparation 2), the compound of the title is obtained.

EXAMPLES 14 TO 18:

Using the procedure described in Example 1, but replacing 2-(2-methoxy-1-naphthyl)ethylamine successively by the compounds of Preparations 3 to 7, the compounds of the following examples are obtained:
EXAMPLE 14: N-[2-(6-HYDROXY-2-METHOXY-1-NAPHTHYL)ETHYL]ACETAMIDE
EXAMPLE 15: N-[2-(2,6-DIPROPOXY-1-NAPHTHYL)ETHYL]ACETAMIDE
EXAMPLE 16: N-[2-(5,6,7,8-TETRAHYDRO-4-METHYL-2-METHOXY-1-NAPHTHYL)ETHYL]ACETAMIDE
EXAMPLE 17: N-[2-(6-METHOXY-1,4-BENZODIOXAN-5-YL)ETHYL]ACETAMIDE
EXAMPLE 18: N-[2-(6-METHOXY-3-METHYLBENZOFURAN-7-YL)ETHYL]ACETAMIDE
EXAMPLE 19: N-[2-(5-METHOXY-4-INDOLYL)ETHYL]ACETAMIDE Using the procedure described in Example 1, but replacing 2-(2-methoxy-1-naphthyl)ethylamine by 2-(5-methoxy-4-indolyl)ethylamine (Bull. Soc. Chim. Fr. 1973, (6) (Pt. 2), pp 2046–2057), the compound of the title is prepared.

EXAMPLES 20 TO 22:

Using the procedure described in Examples 2 to 4, but replacing 2-(2-methoxy-1-naphthyl)ethylamine by 2-(5-methoxy-4-indolyl)ethylamine and using the appropriate chlorides or anhydrides, the compounds of the following examples are successively obtained:
EXAMPLE 20: N-[2-(5-METHOXY-4-INDOLYL)ETHYL]PROPIONAMIDE
EXAMPLE 21: N-[2-(5-METHOXY-4-INDOLYL)ETHYL]CYCLOPROPYLCARBOXAMIDE
EXAMPLE 22: N-(2-(5-METHOXY-4-INDOLYL)ETHYL]TRIFLUOROACETAMIDE
EXAMPLE 23: N-[2-(2-HYDROXY-5-NITROPHENYL)ETHYL]CYCLOPROPYLCARBOXAMIDE Using the procedure described in Example 3, but replacing 2-(2-methoxy-1-naphthyl)ethylamine by 2-(2-hydroxy-5-nitrophenyl)ethylamine (Tetrahedron Letters 1990, vol 31, No. 9, pp 1275–1278), the compound of the title is obtained.
EXAMPLE 24: N-[2-(5-BROMO-2-METHOXYPHENYL)ETHYL]CYCLOPROPYLCARBOXAMIDE Using the procedure described in Example 3, but replacing 2-(2-methoxy-1-naphthyl)ethylamine by 2-(5-bromo-2-methoxyphenyl)ethylamine (Preparation 8), the compound of the title is obtained.

EXAMPLES 25 TO 27:

Using the procedure described in Example 24, but with the appropriate acyl chlorides, the compounds of the following examples are obtained:

EXAMPLE 25: N-[2-(5-BROMO-2-METHOXYPHENYL) ETHYL]CYCLOBUTYLCARBOXAMIDE

EXAMPLE 26: N-[2-(5-BROMO-2-METHOXYPHENYL) ETHYL]CYCLOHEXYLCARBOXAMIDE

EXAMPLE 27: N-[2-(5-BROMO-2-METHOXYPHENYL) ETHYL]CYCLOPENTYLPROPIONAMIDE

EXAMPLE 28: N-[2-(2-METHOXY-1-NAPHTHYL)-1-METHYLETHYL]ACETAMIDE 0.37 g ($1.72 \times 10^{-3}$ mol) of the amine obtained in Preparation 9 and 20 cm$^3$ of anhydrous dichloromethane are introduced under an inert atmosphere into a 100-cm$^3$ two-necked flask. The mixture is stirred and cooled, then 0.32 cm$^3$ ($2.29 \times 10^{-3}$ mol) of triethylamine dried over potassium hydroxide and lastly 0.13 cm$^3$ ($1.84 \times 10^{-3}$ mol) of acetyl chloride are introduced. The ice is then removed and reaction is allowed to proceed at room temperature for ½ hour. Hydrolysis is carried out by pouring the mixture into a stirred waterbath. After separation of the two phases, the aqueous phase is washed twice with CH$_2$Cl$_2$ and the combined organic phases are dried over MgSO$_4$. After evaporation of the latter phases to dryness, the residue is purified by chromatography on a silica column (eluent: MeOH/CH$_2$Cl$_2$, 2:98), and 0.4 g ($1.55 \times 10^{-3}$ mol) of white crystals of the expected acetamide is recovered, equivalent to a 90% yield.

Melting point: 151±3° C.

EXAMPLES 29 TO 34

Using the procedure described in Example 28, but replacing acetyl chloride by the appropriate acyl chloride or anhydride, the compounds of the following examples are obtained:

EXAMPLE 29: N-[2-(2-METHOXY-1-NAPHTHYL)-1-METHYLETHYL]PROPIONAMIDE

Melting point: 133±3° C.

Elemental analysis:

| | |
|---|---|
| C theo = 75.24% | C exp = 74.98% |
| H theo = 7.80% | H exp = 7.91% |
| N theo = 5.16% | N exp = 5.10% |

EXAMPLE 30: N-[2-(2-METHOXY-1-NAPHTHYL)-1-METHYLETHYL]TRIFLUOROACETAMIDE

Melting point: 123±3° C.

Elemental analysis:

| | |
|---|---|
| C theo = 61.73% | C exp = 61.54% |
| H theo = 5.18% | H exp = 5.29% |
| N theo = 4.50% | N exp = 4.40% |

EXAMPLE 31: N-[2-(2-METHOXY-1-NAPHTHYL)METHYLETHYL]CYCLOPROPYLCARBOXAMIDE

EXAMPLE 32: N-[2-(2-METHOXY-1-NAPHTHYL)-1-METHYLETHYL]BUTYRAMIDE

EXAMPLE 33: N-[2-(2-METHOXY-1-NAPHTHYL)-1-METHYLETHYL]PENTANAMIDE

EXAMPLE 34: N-[2-(2-METHOXY-1-NAPHTHYL)-1-METHYLETHYL]CYCLOBUTYLCARBOXAMIDE

EXAMPLE 35: N-[2-(2-METHOXY-5-METHYLPHENYL)ETHYL]ACETAMIDE 0.31 g ($1.54 \times 10^{-3}$ mol) of the hydrochloride of the amine obtained in Preparation 10, which is solubilized in approximately 15 cm$^3$ of water, is introduced into a 100-cm$^3$ two-necked flask. The mixture is stirred, 1.6 g ($19.51 \times 10^{-3}$ mol) of sodium acetate are added and 3.6 cm$^3$ ($38.15 \times 10^{-3}$ mol) of acetic anhydride are then added with a syringe. Reaction is allowed to proceed at room temperature for 30 min. The product formed is extracted from the aqueous phase three times with CH$_2$Cl$_2$. This organic phase is thereafter washed with saturated NaHCO$_3$ solution and then with water, and lastly dried over MgSO$_4$ and evaporated to dryness. The crude product obtained is purified by chromatography in a silica column (eluent: 5% MeOH, 95% CH$_2$Cl$_2$), and 0.25 g ($1.206 \times 10^{-3}$ mol) of the expected acetamide is then obtained, equivalent to a 79% yield.

Melting point: 76°±3° C.

Elemental analysis:

| | |
|---|---|
| C theo = 69.54% | C exp = 69.36% |
| N theo = 6.76% | N exp = 6.72% |
| H theo = 8.27% | H exp = 8.40% |

EXAMPLE 36: N-[2-(2-METHOXY-5-METHYLPHENYL)ETHYL]PROPIONAMIDE

Conversion to the free amine:

In an Erlenmeyer, 0.32 g ($1.59 \times 10^{-3}$ mol) of hydrochloride of the amine obtained in Preparation 10 is solubilized with water, and 2 equivalents of 2N sodium hydroxide, equivalent to 1.59 cm$^3$, are added. The free amine is extracted three times with CH$_2$Cl$_2$; the organic phase is washed wish water, then dried over MgSO$_4$ and lastly evaporated to dryness.

Acylation of the amine:

The amine obtained is introduced into a 1-cm$^3$ three-necked flask and solubilized in 20 cm$^3$ of anhydrous dichloromethane. The mixture under argon is stirred and cooled with an ice bath. 0.33 cm$^3$ ($2.36 \times 10^{-3}$ mol) of triethylamine is then introduced, followed by 0.17 cm$^3$ ($1.96 \times 10^{-3}$ mol) of propionyl chloride added slowly. Reaction is then allowed to proceed at room temperature for 30 min. Hydrolysis is performed by pouring the reaction mixture into water. The expected organic product is extracted three times with dichloromethane, and the combined organic phases are dried over MgSO$_4$ and then evaporated to dryness. The solid residue obtained is purified by chromatography on a silica column (eluent: MeOH/CH$_2$Cl$_2$, 5:95). 0.30 g ($1.36 \times 10^{-3}$ mol) of the expected propionamide (white solid) is then obtained, equivalent to an 85% yield.

Melting point: 70±3° C.

Elemental analysis:

| | |
|---|---|
| C theo = 70.56% | C exp = 70.32% |
| H theo = 8.65% | H exp = 8.79% |
| N theo = 6.33% | N exp = 6.24% |

EXAMPLE 37: N-[2-(2-METHOXY-5-METHYLPHENYL)ETHYL]TRIFLUOROACETAMIDE

Conversion of the hydrochloride to the free amine is carried out in the same manner as in Example 36, starting with 0.35 g ($1.74 \times 10^{-3}$ mol) of hydrochloride. The amine obtained is introduced into a 100-cm$^3$ three-necked flask and solubilized with 20 cm$^3$ of anhydrous dichloromethane. The mixture is stirred under an inert atmosphere and cooled with an ice bath, and 0.14 cm$^3$ ($1.73 \times 10^{-3}$ mol) of pyridine dried over potassium hydroxide is introduced, followed by 0.29 cm$^3$ ($2.05 \times 10^{-3}$ mol) of trifluoroacetic anhydride. Reaction is then allowed to proceed at room temperature for 30 min.

The excess anhydride is hydrolyzed by pouring the reaction mixture into stirred water, and then, after separation of the two phases, the expected organic product is extracted three times with $CH_2Cl_2$. The resulting organic phase is washed with saturated $NaHCO_3$ solution and then with water, dried over $MgSO_4$ and evaporated to dryness. The residue obtained is purified by chromatography on a silica column (eluent: $MeOH/CH_2Cl_2$, 2:98). 0.34 g ($1.30\times10^{-3}$ mol) of the expected amide is finally obtained, equivalent to a 75% yield.

Melting point: 77°±3° C.

Elemental analysis:

| C theo = 55.17% | C exp = 55.27% |
|---|---|
| H theo = 5.40% | H exp = 5.46% |
| N theo = 5.36% | N exp = 5.30% |

EXAMPLES 38 TO 40

Using the procedure described in Example 36, but replacing propionyl chloride by the appropriate acyl chloride, the compounds of the following examples are obtained:

EXAMPLE 38: N-[2-(2-METHOXY-5-METHYLPHENYL)ETHYL]BUTYRAMIDE

EXAMPLE 39: N-[2-(2-METHOXY-5-METHYLPHENYL)ETHYL]CYCLOPROPYLCARBOXAMIDE

EXAMPLE 40: N-[2-(2-METHOXY-5-METHYLPHENYL)ETHYL]HEXANAMIDE

EXAMPLE 41: N-[2-(5-ETHYL-2-METHOXYPHENYL)ETHYL]ACETAMIDE 68.8 mg ($3.19\times10^{-4}$ mol) of hydrochloride of the amine obtained in Preparation 11, which is solubilized with 10 cm$^3$ of water, are introduced into a 50-cm$^3$ three-necked flask, followed by 0.4 g ($4.88\times10^{-3}$ mol) of sodium acetate. The reaction medium is stirred, 0.88 cm$^3$ ($9.33\times10^{-3}$ mol) of acetic anhydride is then added and reaction is allowed to proceed at room temperature for 40 min. The amide formed is extracted from the reaction medium three times with $CH_2Cl_2$. This organic phase is thereafter washed with saturated $NaHCO_3$ solution and then with water, and lastly dried over $MgSO_4$ and evaporated to dryness. The solid residue obtained is purified by chromatography on a silica column (eluent: $MeOH/CH_2Cl_2$, 2:98), and 61.4 mg ($2.78\times10^{-4}$ mol) of the expected amide are recovered, equivalent to an 87% yield.

Melting point: 82°±3° C.

Elemental analysis:

| C theo = 70.56% | C exp = 70.36% |
|---|---|
| H theo = 8.65% | H exp = 8.72% |
| N theo = 6.33% | N exp = 6.23% |

EXAMPLES 42 TO 44:

Using the procedure described in Example 41, but replacing acetic anhydride by the appropriate acyl chloride or anhydride, the compounds of the following examples are obtained:

EXAMPLE 42: N-[2-(5-ETHYL-2-METHOXYPHENYL)ETHYL]PROPIONAMIDE

EXAMPLE 43: N-[2-(5-ETHYL-2-METHOXYPHENYL)ETHYL]CYCLOPROPYLCARBOXAMIDE

EXAMPLE 44: N-[2-(5-ETHYL-2-METHOXYPHENYL)ETHYL]CYCLOBUTYLCARBOXAMIDE

PHARMACOLOGICAL STUDY:

EXAMPLE A: STUDY OF ACUTE TOXICITY

Acute toxicity was assessed after oral administration to groups of 8 mice (26±2 grams). The animals were observed at regular intervals during the first day and daily for two weeks following the treatment. The LD50, causing the death of 50% of the animals, was evaluated.

The $LD_{50}$ of the test products is greater than 1000 mg.kg$^{-1}$ for the compounds of the invention studied, indicating the absence of toxicity of the compounds of the invention.

EXAMPLE B: STUDY OF BINDING TO MELATONIN RECEPTORS

Study of the affinity of the compounds of the invention for melatonin receptors is carried out on chick brain membrane extracts according to the method described by Yuan H. and Pang S. F. (Journal of Endocrinology, (1991), 128, page 475–482).

PROTOCOL:

Dissection of chick brains.

The brains are dissected rapidly at 4° C. and the structures are frozen at −80° C. The frozen structures are then homogenized in a Polytron in 10 volumes of buffer (Tris: 50 mM, pH : 7.4, at 25° C).

After 2 centrifugations at 44,000 g for 25 minutes and at 4° C., the pellets are resuspended in 10 volumes of the same buffer. The quantity of protein is determined by the Folin-Lowry method in the presence of sodium dodecyl sulfate (SDS). The proteins are then fractionated and frozen at −80° C.

MEASUREMENT OF BINDING TO MELATONIN RECEPTORS:

Each assay is carried out in 0.25 cm$^3$ of buffer (50 nM Tris, pH 7.4) and contains 0.15 mg of proteins prepared above, 0.05 nM 2-[$^{125}$I]iodomelatonin and the test compounds at variable concentrations.

Incubation lasts 60 min at 25° C., and the incubation medium is then filtered on a Brandel Cell Harvester® with GF/B filters (Whatman).

The filters are rinsed three times with 4 cm$^3$ of buffer (50 mM Tris, pH 7.4).

Non-specific binding is determined in the presence of $10^{-5}$M melatonin.

The radioactivity is counted with a β counter.

The assays are carried out in triplicate.

RESULTS:

The compounds of the invention possess a very high selective affinity for melatonin receptors, it being possible for this affinity to be higher than that of melatonin itself.

No such noteworthy affinity is encountered with compounds possessing a hydroxyl or alkoxy radical in their structure at the meta or para position with respect to the alkylamide chain on the benzene ring, instead of the ortho position as claimed for the compounds of the invention.

EXAMPLE C: PHARMACEUTICAL COMPOSITION: TABLETS

| Tablets containing a 5 mg dose of N-[2-(2-methoxy-1-naphthyl)ethyl]trifluoroacetamide | |
|---|---|
| N-[2-(2-methoxy-1-naphthyl)ethyl]-trifluoroacetamide | 5 g |
| Wheat starch | 15 g |
| Corn starch | 15 g |
| Lactose | 15 g |
| Magnesium stearate | 2 g |
| Silica | 1 g |
| Hydropropylcellulose | 2 g |

We claim:

1. A compound which is selected from those of formula (I):

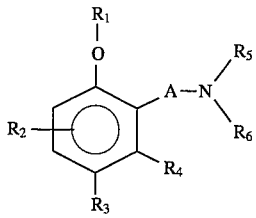

in which:

A represents a —CH$_2$—CH$_2$— chain, unsubstituted or substituted with lower alkyl, R$_1$ represents hydrogen or lower alkyl, R$_2$ represents hydrogen, halogen, or lower alkyl, one of R$_3$ and R$_4$ is hydrogen, the other being lower alkyl, R$_5$ represents hydrogen or lower alkyl, R$_6$ represents a group

in which X represents oxygen and R$_7$ represents a radical chosen from:

lower alkyl, unsubstituted or substituted with one or more radicals chosen from halogen, hydroxyl, and lower alkoxy, linear or branched alkenyl having 2 to 7 carbon atoms, inclusive, unsubstituted or substituted with one or more radicals chosen from halogen, hydroxyl, and lower alkoxy, and —(CH$_2$)$_m$—E$_4$ in which m represents 0 or 1 to 4, inclusive, and E$_4$ represents a mono- or bicyclic cycloalkyl having 3 to 12 carbon atoms, inclusive, unsubstituted or substituted with one or more radicals chosen from halogen, and lower alkyl, with the proviso that R$_7$ can represent lower alkyl, unsubstituted or substituted with one or more radicals chosen from halogen, hydroxyl, and lower alkoxy, only if one of the substituents R$_3$ and R$_4$ represents lower alkyl and the other substituent R$_3$ or R$_4$ represents hydrogen, optical isomers, and addition salts thereof with a pharmaceutically-acceptable acid or base when R$_3$ or R$_4$ represents a salifiable group, on the understanding that the terms "lower alkyl" and "lower alkoxy" denote linear or branched groups having 1 to 6 carbon atoms, inclusive, and that the terms "cycloalkenyl" and "alkenyl" denote hydrocarbon groups containing one or more double bonds.

2. A compound as claimed in claim 1 in which R$_1$ represents a methyl radical.

3. The compound as claimed in claim 1 which is N-[2-(5-ethyl-2-methoxyphenyl)ethyl]propionamide.

4. A pharmaceutical composition containing as active principle a compound as claimed in claim 1, in combination with one or more pharmaceutically-acceptable excipients.

5. A method of treating a mammal afflicted with a sleep disorder comprising the step of administering to the said mammal an amount of a compound selected from those of formula (I):

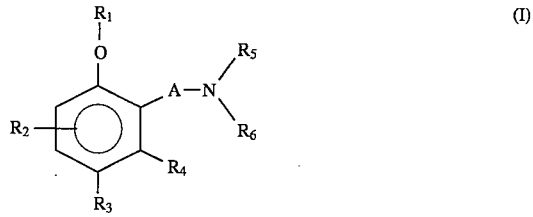

in which:

A represents a —CH$_2$—CH$_2$-chain, unsubstituted or substituted with lower alkyl, R$_1$ represents hydrogen or lower alkyl, R$_2$ represents hydrogen, halogen, or lower alkyl, R$_3$ and R$_4$, which may be identical or different, each represent, independently of one another, a radical chosen from:
hydrogen,
halogen,
lower alkyl,
cyano,
carboxyl,
nitro,
amino,
lower alkylamino,
di(loweralkyl)amino,
—(CH$_2$)$_n$—E$_1$ in which n is 0 or 1 to 4, inclusive, and E$_1$ represents cycloalkyl or cycloalkenyl and contains 3 to 8 carbon atoms, inclusive, E$_1$ being unsubstituted or substituted with one or more radicals chosen from halogen, oxo, and lower alkyl,
and —(CH$_2$)$_{n'}$—E$_2$ in which n' is 0 or 1 to 4, inclusive, and E$_2$ represents a radical chosen from: phenyl, naphthyl, pyrrolyl, thienyl, furyl, pyridyl, pyrazinyl, pyrimidinyl, pyridazinyl, quinolyl, and isoquinolyl, E$_2$ being unsubstituted or substituted with one or more radicals chosen from: halogen, hydroxyl, lower alkyl, lower alkoxy, and trifluoromethyl, R$_5$ represents hydrogen or lower alkyl, R$_6$ represents a group

in which X represents oxygen and R$_7$ represents a radical chosen from:
lower alkyl, unsubstituted or substituted with one or more radicals chosen from halogen, hydroxyl, and lower alkoxy,
linear or branched alkenyl having 2 to 7 carbon atoms, inclusive, unsubstituted or substituted with one or more radicals chosen from halogen, hydroxyl, and lower alkoxy,
and —(CH$_2$)$_m$—E$_4$ in which m represents 0 or 1 to 4, inclusive, and E$_4$ represents a mono-or bicyclic cycloalkyl having 3 to 12 carbon atoms, inclusive, unsubstituted or substituted with one or more radicals chosen from halogen and lower alkyl, with the proviso that $R_7$ can represent lower alkyl, unsubstituted or substituted with one or more radicals chosen from halogen, hydroxyl, and lower alkoxy, only if one of the substituents $R_3$ and $R_4$ represents lower alkyl and the other substituent $R_3$ or $R_4$ represents hydrogen, its optical isomers, and addition salts thereof with a pharmaceutically-acceptable acid or base when $R_3$ or $R_4$ represents a salifiable group, on the understanding that the terms "lower alkyl" and "lower alkoxy" denote linear or branched groups having 1 to 6 carbon atoms, inclusive, and that the terms "cycloalkenyl" and "alkenyl" denote hydrocarbon groups containing one or more double bonds, which binds at melatonin receptors and is effective in the treatment of said disorder.

6. The method of claim 5 wherein the compound is N-[2-(5-ethyl-2-methoxyphenyl)ethyl]propionamide.

* * * * *

UNITED STATES PATENT AND TRADEMARK OFFICE
CERTIFICATE OF CORRECTION

PATENT NO. : 5,604,261
DATED : Feb. 18, 1997
INVENTOR(S) : Michel Langlois, Pierre Renard, Gerard Adam It is certified that error appears in the above-indentified patent and that said Letters Patent is hereby corrected as shown below:

Column 2, line 44: "understanding that she" should read -- understanding that the --; and "Lower" at end of the line should read -- lower --.

Column 3, line 18: "she" should read -- the --.

Column 4, line 64: "adore" should read -- above --.

Column 11, line 54: Insert -- - -- (dash) between "2" and "methoxybenzene" at the beginning of the line.

Column 14, line 4: "1.7g (0.54x10$^{-3}$ mol)" should read -- 1.7g (10.54x10$^{-3}$ mol) --; and "nitrite" should read -- nitrile --.

Column 14, line 23: "C exp 39.39%" should read -- C exp 59.39% --.

Column 14, line 36: Delete the "-" at the end of the line and <u>insert</u> -- ) --.

Column 14, line 37: Delete the ")" at the beginning of the line.

Column 14, line 48: "Then" should read -- then --.

UNITED STATES PATENT AND TRADEMARK OFFICE
CERTIFICATE OF CORRECTION

PATENT NO. : 5,604,261
DATED : Feb. 18, 1997
INVENTOR(S) : Michel Langlois, Pierre Renard, Gerard Adam It is certified that error appears in the above-indentified patent and that said Letters Patent is hereby corrected as shown below:

Column 15, line 18: "(atom.)," should read -- (arom.), --.

Column 15, line 51: "(atom.)," should read -- (arom.), --.

Column 16, line 63: "(atom.)," should read -- (arom.), --.

Column 16, line 64: "(atom.)," should read -- (arom.), --.

Column 19, line 58: Delete the "M" at the end of the line.

Column 19, line 59: Insert -- M -- at the beginning of the line to read -- METHYLETHYL) --.

Column 20, line 31: "wish" should read -- with --.

UNITED STATES PATENT AND TRADEMARK OFFICE
CERTIFICATE OF CORRECTION

PATENT NO. : 5,604,261
DATED : Feb. 18, 1997
INVENTOR(S) : Michel Langlois, Pierre Renard, Gerard Adam It is certified that error appears in the above-indentified patent and that said Letters Patent is hereby corrected as shown below:

Column 22, line 8: "LD50," should read -- $LD_{50}$ --.

Column 23, line 58: Insert -- its -- at the beginning of the line.

Signed and Sealed this

Fourteenth Day of October, 1997

Attest:

BRUCE LEHMAN

*Attesting Officer*     *Commissioner of Patents and Trademarks*